(12) United States Patent
Cronenberg

(10) Patent No.: US 9,844,629 B2
(45) Date of Patent: Dec. 19, 2017

(54) INJECTION DEVICE

(75) Inventor: Richard Cronenberg, Mahwah, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 988 days.

(21) Appl. No.: 14/117,838

(22) PCT Filed: May 18, 2011

(86) PCT No.: PCT/US2011/000878
§ 371 (c)(1),
(2), (4) Date: Nov. 14, 2013

(87) PCT Pub. No.: WO2012/158136
PCT Pub. Date: Nov. 22, 2012

(65) Prior Publication Data
US 2014/0081239 A1 Mar. 20, 2014

(51) Int. Cl.
*A61M 5/20* (2006.01)
*A61M 5/28* (2006.01)
(Continued)

(52) U.S. Cl.
CPC ........ *A61M 5/2033* (2013.01); *A61M 5/2429* (2013.01); *A61M 5/286* (2013.01);
(Continued)

(58) Field of Classification Search
CPC .. A61M 5/2033; A61M 5/326; A61M 5/2429; A61M 5/282; A61M 2005/206; A61M 2005/2073
See application file for complete search history.

(56) References Cited

U.S. PATENT DOCUMENTS 4,188,950 A 2/1980 Wardlaw
4,196,732 A 4/1980 Wardlaw
(Continued)

FOREIGN PATENT DOCUMENTS

CN 1635919 A 7/2005
EP 0388169 A2 9/1990
(Continued)

*Primary Examiner* — Laura Bouchelle
(74) *Attorney, Agent, or Firm* — Dickinson Wright PLLC

(57) ABSTRACT

An injection device (100), including a base (104), a sliding body (116) slidably connected to the base (104), a double-ended needle (120) fixed to the sliding body (116), a biasing member (124) for proximally biasing the sliding body (116) with respect to the base (104), and for retracting the needle (120) into the device (100) subsequent to activation of the device (100), a medicament cartridge (128) for holding a medicament, slidably connected to the sliding body (116), and a stopper (132) slidably disposed within the medicament cartridge (128). The base (104) has a proximal end (108) and a surface (164) disposed at a distal end (112) thereof for contacting a patient's skin. The base (104) also has a first locking mechanism. The sliding body, (116) has a locking feature and a second locking mechanism. The second locking mechanism locks the medicament cartridge (128) relative to the sliding body (116) upon completion of displacement of the medicament cartridge (128) relative to the sliding body (116). The first locking mechanism and the locking feature interact to lock the sliding member (116) relative to the base subsequent to retraction of the needle (120) into the device (100).

20 Claims, 9 Drawing Sheets

(51) Int. Cl.
  *A61M 5/50*   (2006.01)
  *A61M 5/24*   (2006.01)
  *A61M 5/32*   (2006.01)
  *A61M 5/00*   (2006.01)

(52) U.S. Cl.
  CPC .............. *A61M 5/326* (2013.01); *A61M 5/50* (2013.01); *A61M 5/5066* (2013.01); *A61M 5/002* (2013.01); *A61M 5/3271* (2013.01); *A61M 2005/2407* (2013.01); *A61M 2005/247* (2013.01); *A61M 2005/3247* (2013.01); *A61M 2005/3267* (2013.01)

(56) References Cited

U.S. PATENT DOCUMENTS

| | | | |
|---|---|---|---|
| 4,214,584 A | 7/1980 | Smirnov et al. | |
| 4,227,528 A | 10/1980 | Wardlaw | |
| 4,258,713 A | 3/1981 | Wardlaw | |
| 4,378,015 A | 3/1983 | Wardlaw | |
| 4,747,831 A | 5/1988 | Kulli | |
| 4,767,413 A | 8/1988 | Haber et al. | |
| 4,813,426 A | 3/1989 | Haber et al. | |
| 4,850,961 A | 7/1989 | Wanderer et al. | |
| 4,894,054 A | 1/1990 | Miskinyar | |
| 4,900,310 A | 2/1990 | Ogle | |
| 4,955,871 A | 9/1990 | Thomas | |
| 5,019,048 A | 5/1991 | Margolin | |
| 5,248,303 A | 9/1993 | Margolin | |
| 5,267,963 A | 12/1993 | Bachynsky | |
| 5,425,722 A | 6/1995 | Whisson | |
| 5,498,245 A | 3/1996 | Whisson | |
| 5,599,309 A | 2/1997 | Marshall et al. | |
| 5,634,906 A | 6/1997 | Haber et al. | |
| 7,621,891 B2 | 11/2009 | Wyrick | |
| 7,645,265 B2 | 1/2010 | Stamp | |
| 7,670,314 B2 | 3/2010 | Wall et al. | |
| 7,981,085 B2 | 7/2011 | Ethelfeld et al. | |
| 2003/0212362 A1* | 11/2003 | Roser | A61M 5/282 604/110 |
| 2004/0133159 A1 | 7/2004 | Haider et al. | |
| 2007/0017532 A1 | 1/2007 | Wyrick | |
| 2007/0191780 A1* | 8/2007 | Modi | A61M 5/282 604/187 |
| 2007/0293826 A1* | 12/2007 | Wall | A61M 5/19 604/200 |

FOREIGN PATENT DOCUMENTS

| | | |
|---|---|---|
| GB | 2467904 A | 8/2010 |
| GB | 2471304 A | 12/2010 |
| JP | 2002-506695 A | 3/2002 |
| JP | 2003-505159 A | 2/2003 |
| JP | 2007-502156 A | 2/2007 |
| JP | 2007-518507 A | 7/2007 |
| WO | 02/074361 A2 | 9/2002 |
| WO | WO-2005079441 A2 | 9/2005 |
| WO | WO2010035056 A1 | 4/2010 |
| WO | WO-2011117287 A1 | 9/2011 |
| WO | WO-2011149455 A1 | 12/2011 |

* cited by examiner

INJECTION DEVICE

FIELD OF THE INVENTION

The present invention relates generally to an injection device for dispensing a medicament, and more particularly to a low-cost, single use injection device.

BACKGROUND OF THE INVENTION

Various injection devices are known in the art. Many such injection devices, however, require medical training for proper use. In addition, many such injection devices are expensive. Thus, there is a need to provide a low-cost, intuitive injection device that can be properly used by untrained or minimally trained people for self-injection or injection of others. For example such a needed device could be used for inoculations in developing areas of the world where medical care is difficult to obtain, or for a parent to inoculate a child.

SUMMARY OF THE INVENTION

An aspect of the present invention is to provide a low-cost injection device. Another aspect of the present invention is to provide an intuitive injection device that can be properly used by untrained or minimally trained people for self-injection or injection of others.

The foregoing and/or other aspects of the present invention are achieved by providing an injection device, including a base, a sliding body slidably connected to the base, a double-ended needle fixed to the sliding body, a biasing member for proximally biasing the sliding body with respect to the base, and for retracting the needle into the device subsequent to activation of the device, a medicament cartridge for holding a medicament, slidably connected to the sliding body, and a stopper slidably disposed within the medicament cartridge. The base has a proximal end and a surface disposed at a distal end thereof for contacting a patient's skin. The base also has a first locking mechanism. The sliding body has a locking feature and a second locking mechanism. The second locking mechanism locks the medicament cartridge relative to the sliding body upon completion of displacement of the medicament cartridge relative to the sliding body. The first locking mechanism and the locking feature interact to lock the sliding member relative to the base subsequent to retraction of the needle into the device.

The foregoing and/or other aspects of the present invention are also achieved by providing an injection device, including a base having a proximal end and a surface disposed at a distal end thereof for contacting a patient's skin, the base comprising a plurality of angled lips and a plurality of axial ribs, each plurality being disposed circumferentially about an interior of the base, a sliding body slidably connected to the base, the sliding body comprising a holding rib protruding radially inward and a plurality of circumferentially disposed, distally depending, cantilevered legs, each leg having a pair of feet circumferentially protruding from a distal end thereof, and a double-ended needle fixed to the sliding body. The device also includes a biasing member for proximally biasing the sliding body with respect to the base, and for retracting the needle into the device subsequent to activation of the device, a medicament cartridge for holding a medicament, the medicament cartridge being slidably connected to the sliding body and having a cartridge lip protruding radially outward from a distal end thereof, the cartridge lip being disposed adjacent to the holding rib prior to activation of the device, and a stopper slidably disposed within the medicament cartridge. A force applied to the medicament cartridge to displace the cartridge lip distally past the holding lip exceeds a force applied to the medicament cartridge to displace the feet distally past the angled lips and drive the needle into a patient's skin.

The foregoing and/or other aspects of the present invention are also achieved by providing a method for injecting a medicament in a patient using an injection device having a base, a sliding body slidably connected to the base, a double-ended needle fixed to the sliding body, a biasing member, a medicament cartridge for holding a medicament, the medicament cartridge being slidably connected to the sliding body, and a stopper slidably disposed within the medicament cartridge. The method includes pressing the medicament cartridge toward the patient's skin/injection site to sequentially distally displace the sliding body relative to the base, insert the needle into the patient, and compress the spring, puncture the stopper with the needle to establish fluid communication between the needle and the medicament cartridge, and proximally displace the stopper relative to the medicament cartridge to eject the medicament from the medicament cartridge. The method also includes, subsequent to ejecting the medicament from the medicament cartridge, ceasing pressure on the medicament cartridge to sequentially proximally displace the sliding body relative to the base to withdraw the needle from the patient due to the force of the spring, and lock the sliding member relative to the base to prevent reuse of the device.

Additional and/or other aspects and advantages of the present invention will be set forth in part in the description that follows and, in part, will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which.

DETAILED DESCRIPTION OF EXEMPLARY EMBODIMENTS

Figure 1:
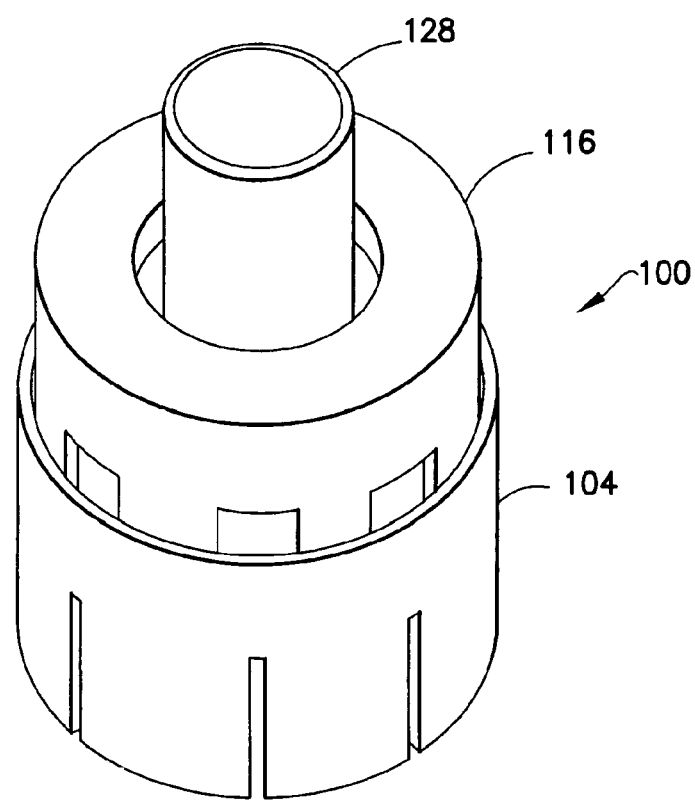
FIG. 1 is a perspective view of an injection device in accordance with an embodiment of the present invention.

Reference will now be made in detail to embodiments of the present invention, examples of which are illustrated in the accompanying drawings, wherein like reference numerals refer to the like elements throughout. The descriptions of these embodiments exemplify the present invention by referring to the drawings.

Figure 2:
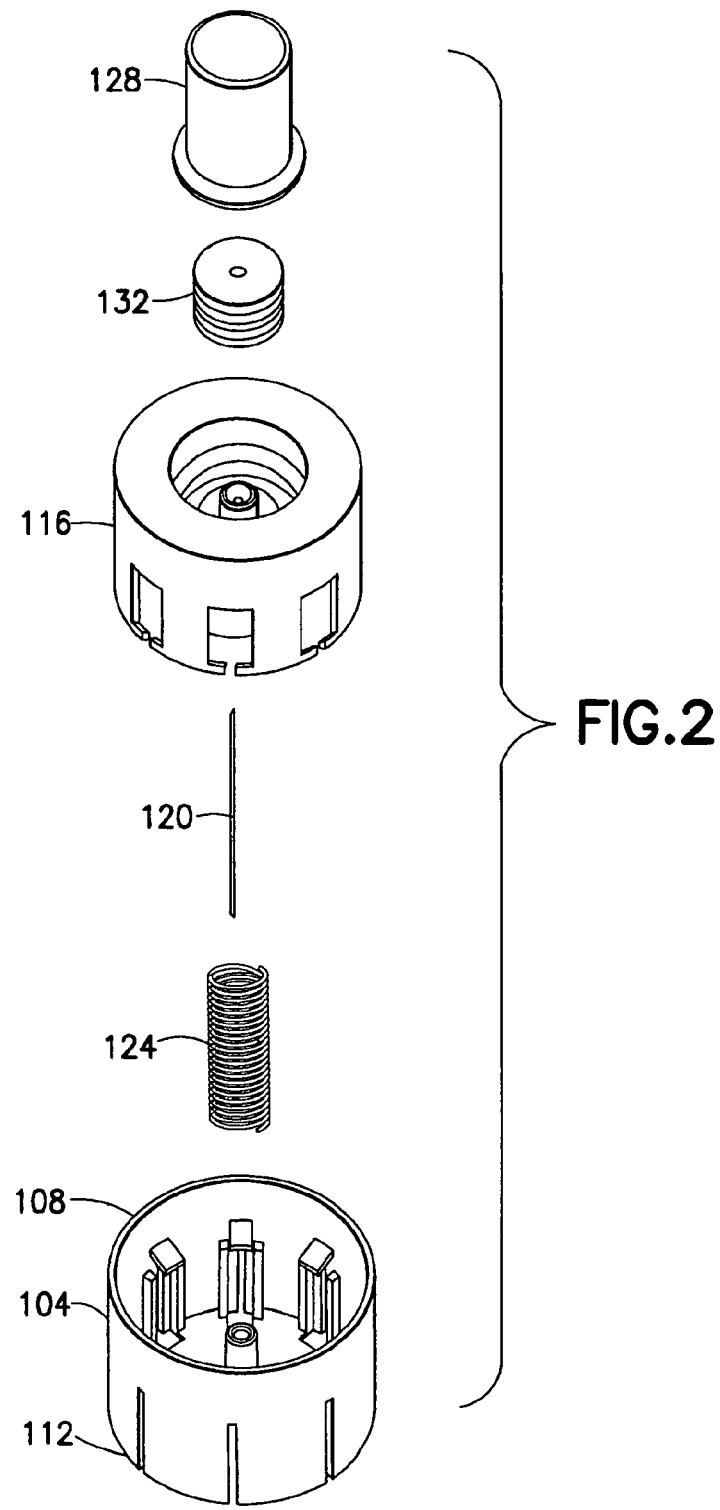
FIG. 2 is a perspective exploded view of the device of FIG. 1.

FIG. 1 is a perspective view of an injection device 100 in accordance with an embodiment of the present invention and FIG. 2 is a perspective exploded view of the device 100. As shown in FIGS. 1 and 2, the injection device 100 includes a base 104 that has a proximal end 108 and a distal end 112, a sliding body slidably connected to the base 104, a double ended needle 120 fixed to the sliding body 116, and a biasing member 124 (such as a spring) for proximally biasing the sliding body 116 respect the base 104 and, as will be discussed in greater detail below, for retracting the needle 120 into the device 100 subsequent to activation thereof.

The device 100 also includes a medicament cartridge 128 for holding the medicament. The medicament cartridge 128 is slidably connected to the sliding body 116. According to one embodiment, the medicament cartridge 128 is made of glass. According to another embodiment, the medicament cartridge 128 is made of a transparent plastic material that does not react with the medicament. Examples of such a plastic material include, but are not limited to, cyclic olefin polymer (COP) and cyclic olefin copolymer (COC). One example of a COC is available from Zeon Chemicals, L.P., of Louisville, Ky. under the designation "BD CCP Resin," and is listed by the U.S. Food and Drug Administration as DMF No. 16368.

In addition, the device includes a stopper 132 slidably disposed within the medicament cartridge 128, for retaining the medicament within the medicament cartridge 128 and expelling the medicament from the medicament cartridge 128. In combination, the medicament cartridge 128 and the stopper 132 disposed therein define a medicament chamber therebetween. According to one embodiment, the stopper 132 is made of an elastomeric material, such as rubber, that does not react with the medicament.

In one embodiment, the medicament cartridge 128 is pre-assembled to the remainder of the device 100, and the entire device 100 is provided to the user in sterile packaging, for example a cup with a foil top. According to another embodiment, a pre-filled medicament cartridge 128 (including the stopper 132) is provided separately from the remainder of the device 100. In such an embodiment, the medicament cartridge 128 can be assembled to the remainder of the device 100 at the time of the injection, and thus, is, selectively connectable to the sliding body 116, as described in greater detail below. Refrigeration space may be at a premium in developing areas of the world. For medicament that needs to be refrigerated, such a design provides for more efficient use of the refrigeration space because only the medicament cartridge 128 is refrigerated, not the entire device 100.

Figure 3:
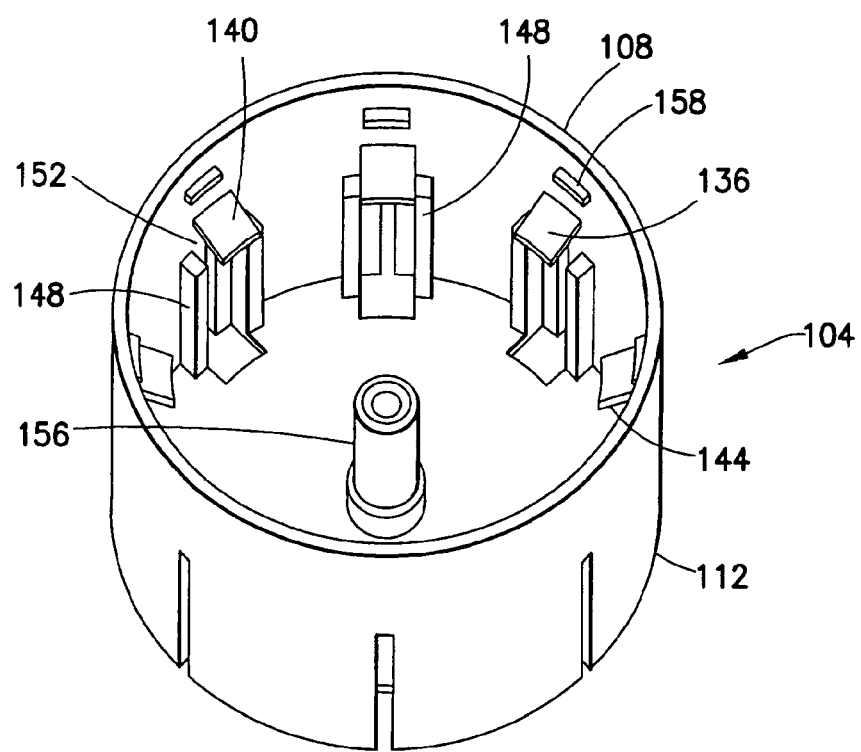
FIGS. 3 and 4 are perspective views of a base of the device of FIG. 1.
Figure 4:
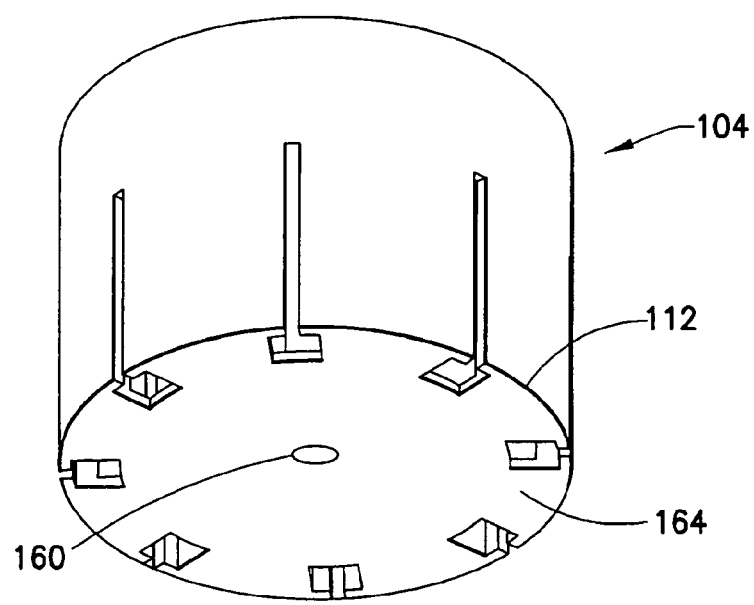

FIGS. 3 and 4 are respective perspective views of proximal and distal ends 108 and 112 of the base 104. As shown in FIG. 3, the base 104 has a plurality of angled lips 136 disposed circumferentially about interior of the base 104. Each of the angled lips 136 projects radially inward, and is angled distally with respect to the base 104. In addition, each angled lip 136 has a proximal angled surface 140 and a distal angled surface 144. The base 104 also includes a plurality of axial ribs 148 circumferentially disposed about the interior of the base 104. The axial ribs 148 are distally separated from the angled lips 136 to define a locking space 152 therebetween. According to on embodiment, a pair of axial ribs 148 corresponds to each angled lip 136 and the individual ribs 148 of the pair are circumferentially disposed on opposing sides of the corresponding angled lip 136. Collectively, the angled lips 136 and the axial ribs 148 (as well as the locking space 152 disposed therebetween) form a first locking mechanism, which is discussed in greater detail below.

The base 104 additionally includes a central boss 156 with a central bore 160 through which the needle 120 moves. In addition, as will be described in greater detail below, according to one embodiment, the base 104 includes a plurality of base locking ribs 158 for connecting the sliding body 116 and the base 104 prior to activation of the device 100.

As shown in FIG. 4, the distal end of the base 112 has a surface 164 for contacting a patient's skin. According to one embodiment, the surface 164 is flat. According to another embodiment, the surface 164 is concave, or proximally domed, for example, to stably contact the patient's skin. One skilled in the art will understand that the surface 164 may be convex, have another shape, or have a plurality of shapes without departing from the scope of the invention. According to one embodiment, at least a portion of the surface 164 has an adhesive disposed thereon for temporarily adhering the device 100 to the patient's skin. Such an adhesive portion may be covered by, for example, a paper cover which is removed prior to use of the device 100.

Figure 5:
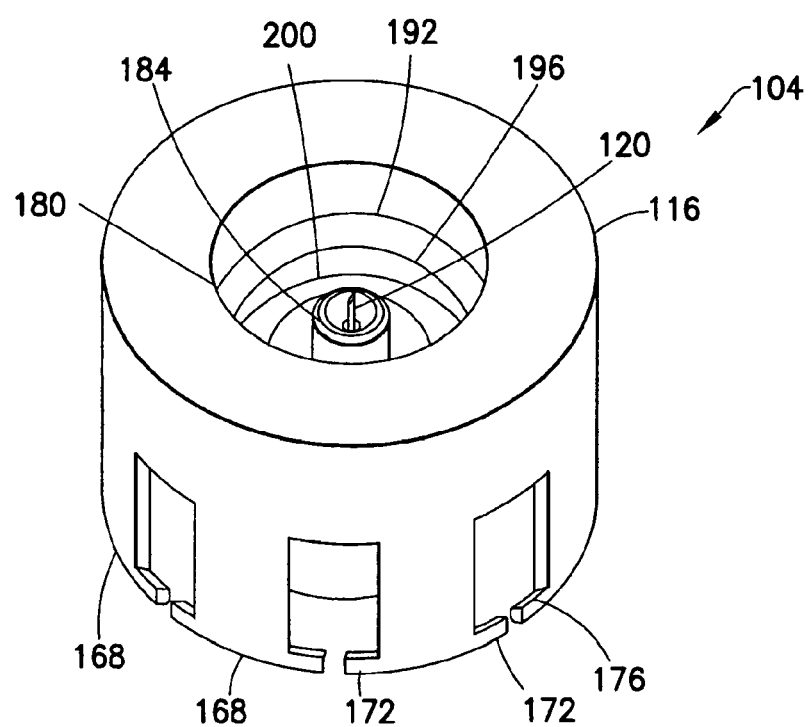
FIGS. 5 and 6 are perspective views of a sliding body of the device of FIG. 1.
Figure 6:
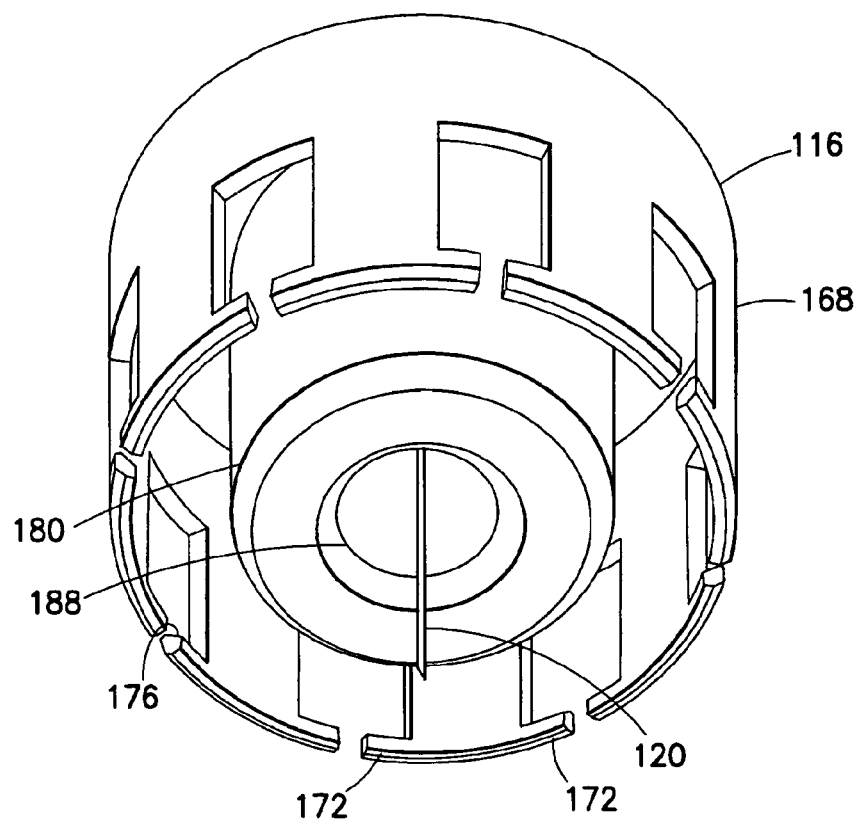

FIG. 5 is a perspective view of proximal ends of the sliding body 116 and the needle 120, and FIG. 6 is a perspective view of the distal ends of the sliding body 116 and the needle 120. According to one embodiment, the needle 120 is fixed to the sliding body 116. In other words, the needle 120 does not displace relative to the sliding body 116. Methods for fixing the needle 120 to the sliding body 116 include gluing, epoxying, insert molding, and swaging, using, for example, heat or ultrasonic energy. One skilled in the art will appreciate that other methods of fixing the needle 120 to the sliding body 116 may be employed without departing from the scope of the invention.

Figure 7:
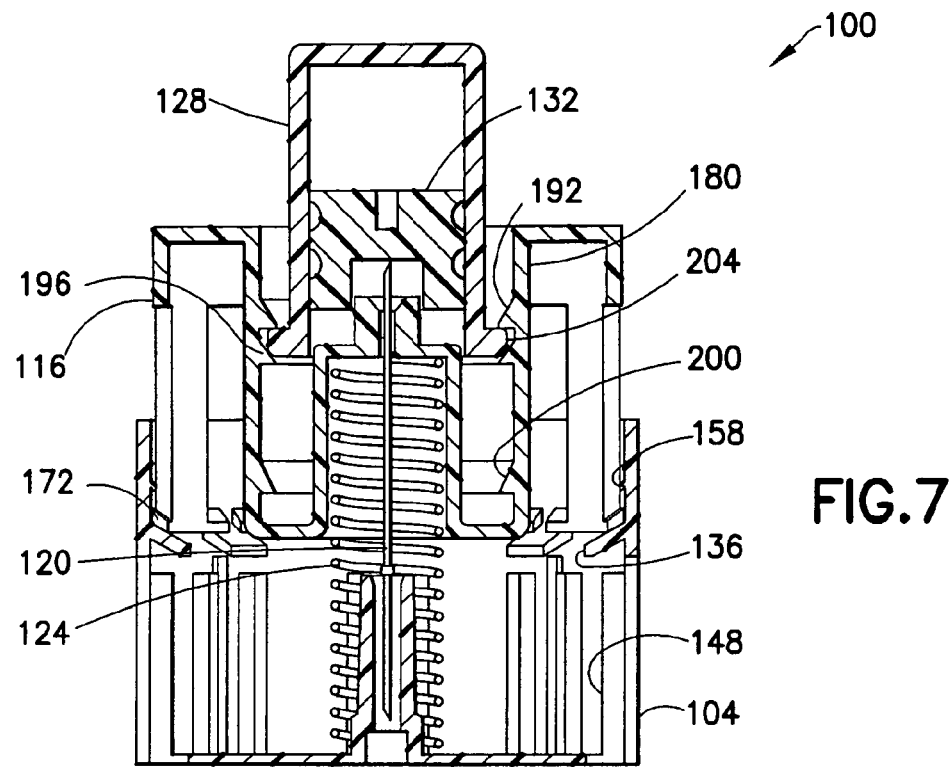
FIG. 7 is a cross-sectional view illustrating a pre-activated state of the device of FIG. 1.

As shown in FIGS. 5-7, the sliding body 116 includes a plurality of circumferentially disposed, distally depending, cantilevered legs 168. According to one embodiment, each leg 168 has a pair of feet 172 circumferentially protruding from a distal end thereof. According to one embodiment, as shown in FIGS. 5 and 6 (although most clearly shown in FIG. 11), proximal surfaces 176 of the feet 172 are angled to correspond to the angle of the distal angled surfaces 144 of the angled lips 136. Collectively, the legs 168 and the feet 172 form a locking feature, which is discussed in greater detail below.

To assemble the sliding body 116 with the base 104, first, the biasing member 124 is inserted into the base 104 around the central boss 156. Subsequently, the sliding body is inserted distally into the base 104 (over the biasing member 124) until the legs 168 and/or the feet 172 elastically deform radially inward and the feet 172 distally pass base locking ribs 158. Subsequently, the legs 168 and/or of the feet 172 spring back radially outward to contact the inner wall of the base 104. According to one embodiment, the base locking ribs 158 are angled to correspond to the angle of the proximal surfaces 176 of the feet 172. Because of the corresponding angles, once the feet 172 distally pass the base locking ribs 158, the base locking ribs 158 engage the proximal surfaces 176 of the feet 172 (due to the force of the biasing member 124, which biases the sliding body 116 proximally relative to the base 104) to prevent proximal movement of the feet 172 past the base locking ribs 158. Such an assembled state is shown, for example, in FIG. 7.

Referring back to FIG. 5, sliding body 116 additionally includes a central portion 180 that has a stopper-receiving boss 184 centrally disposed thereon. The walls of the central portion 180 form a cartridge channel for slidably receiving the medicament cartridge 128. In addition, as shown in FIG. 6, the central portion 180 has an opening 188 at a distal end thereof for receiving the central boss 156 of the base 104 and the biasing member 124. Referring to FIGS. 5 and 7, the central portion 180 has a series of ribs disposed therein, specifically, a connecting rib 192, a holding rib 196, and a locking rib 200. As discussed in greater detail below, the locking rib 200 forms a second locking mechanism. During operation of the device 100, the ribs 192, 196, and 200 interact with a cartridge lip 204, which protrudes radially outward from the distal end of the medicament cartridge 128. According to one embodiment, the ribs 192, 196, and 200 are annular.

According to another embodiment, the connecting rib 192, for example, includes a plurality of connecting ribs 192 circumferentially spaced from each other about the central portion 180. In other words, rather than a solid ring, the plurality of connecting ribs 192 are disposed to form a segmented array with spaces between the segments. Such an embodiment may reduce the amount of force necessary to distally advance the cartridge lip 204 past the connecting ribs 192. For example, if the medicament cartridge 128 is made of glass, and thus, is relatively inflexible, the reduced force required to advance the cartridge lip 204 past the plurality of discrete connecting ribs 192 may be advantageous. Regardless of the choice of materials for the medicament cartridge 128, though, one skilled in the art will appreciate that various combinations of annular rings and ring segments may be respectively used for the ribs 192, 196, and 200 without departing from the scope of the invention.

To secure the medicament cartridge 128 to the sliding body 116, a user inserts the medicament cartridge 128 into the central portion 180 of the sliding body 116 until the cartridge lip 204 passes the connecting rib 192 and comes to rest against the holding rib 196, as shown in FIG. 7. In this pre-activated state, the cartridge lip 204 is disposed between the connecting rib hundred 92 and the holding rib 196 and the feet 172 are disposed adjacent to the angled lips 136, as shown in FIG. 7. In this state, the sliding body 116 is in a first, or pre-activated position, in which the needle 120 is disposed entirely within the device 100. According to one embodiment, the force required to distally displace the cartridge lip 204 past the holding lip 196 is greater than the force required to distally displace the cartridge lip 204 past the connecting rib 192. Such an embodiment provides ease of connection of the medicament cartridge 128 with the sliding body 116 but prevents inadvertent activation of the device 100 during connection. According to one embodiment, the holding rib 196 protrudes radially inward further than the connecting rib 192 to provide the force differential. According to another embodiment, the holding rib 196 is less flexible than the connecting rib 192 to provide the force differential.

Figure 8:
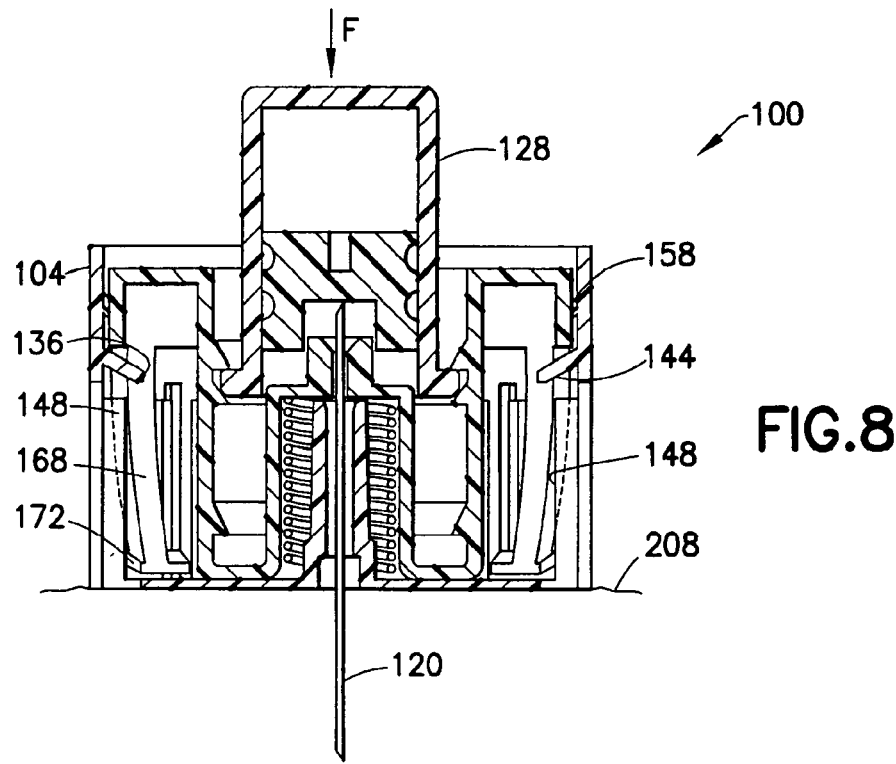
FIGS. 8-11 are cross-sectional views illustrating operation of the device of FIG. 1.

Operation of the device 100 will now be described with respect to FIGS. 7-11. After assembling the device 100 (or removing the pre-assembled device 100 from its packaging) and using an alcohol swab to disinfect an injection site on the patient's skin 208, the user presses the pre-activated device 100 (FIG. 7) against the patient's skin 208 and presses down (i.e., distally) on the medicament cartridge 128. The force required to distally displace the cartridge lip 204 relative to the holding rib 196 is greater than the force required to distally displace the feet 172 relative to the angled lips 136. Additionally, the force required to distally displace the cartridge lip 204 relative to the holding rib 196 is greater than the force required to compress the biasing member 124 and pierce the patient's skin 208 with the distal end of the needle 120. Accordingly, as shown in FIG. 8, when the user presses down on the medicament cartridge 128, the force is transferred to the sliding body 116 and the legs 168 and/or the feet 172 elastically deform radially inward, thereby allowing the feet 172 to distally pass the angled lips 136. The legs 168 and/or the feet 172 then snap back radially outward and the slide distally along the axial ribs 148. In addition, the sliding body 116 compresses the biasing member 124 and drives the needle 120 to a predetermined depth into the patient's skin 208. In this second, or activated position of the sliding body 116, a portion of the needle 120 extends outside of the device 100.

Figure 9:
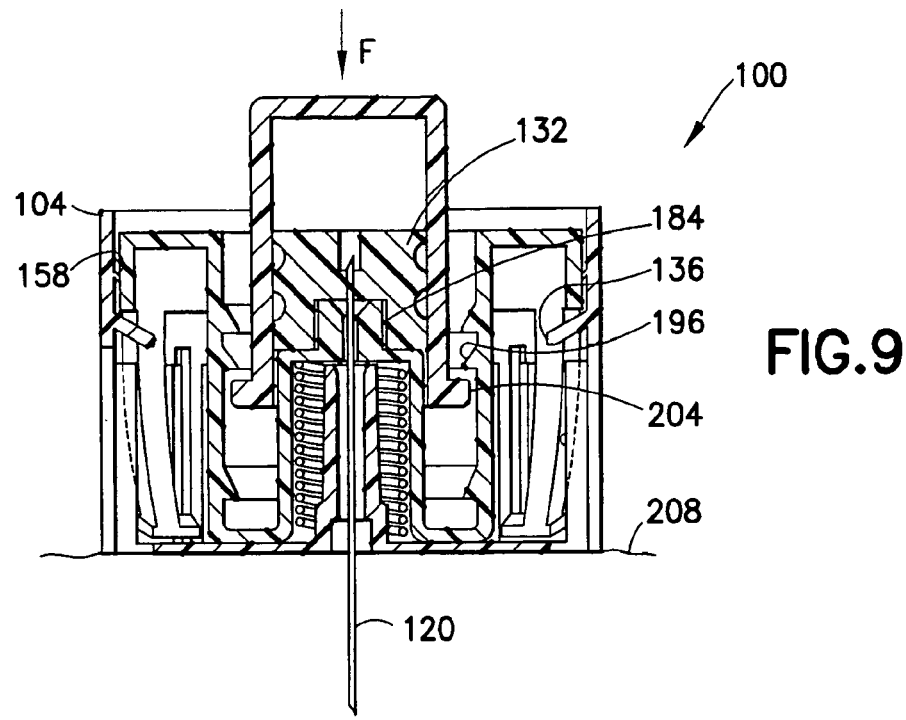
Figure 10:
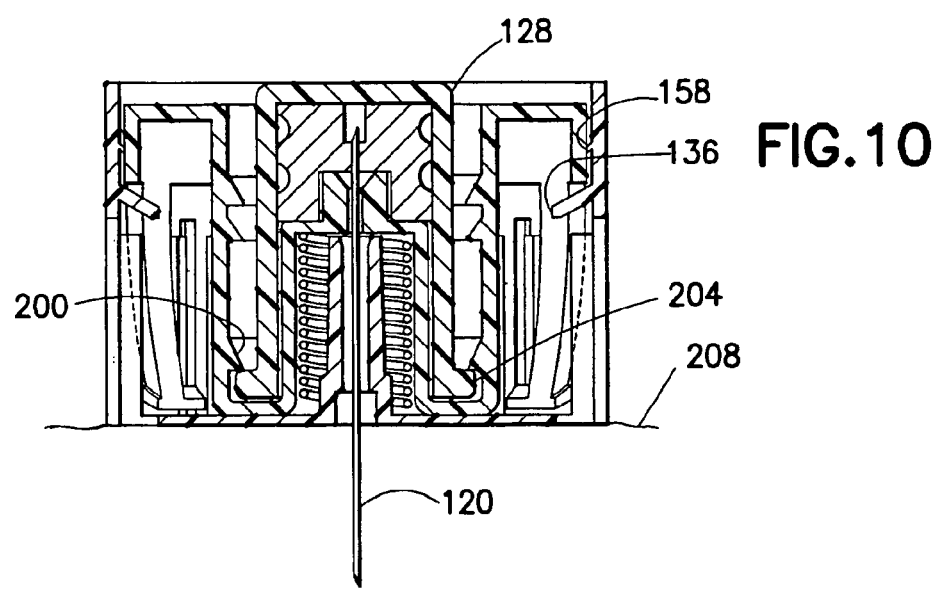

As the user continues to depress the medicament cartridge 128, the cartridge lip 204 distally passes the holding rib 196 and the medicament cartridge 128 and the stopper travel distally in the cartridge channel, seating the stopper 132 on the stopper-receiving boss 184. This action also pierces the stopper 132 with the proximal end of the needle 120, thereby establishing fluid communication between the medicament and the needle 120, as shown in FIG. 9. Thus, the stopper 132 is selectively pierceable by the needle 120 to establish communication with the medicament. As the user continues to press down on the medicament cartridge 128, as shown in FIG. 10, the medicament cartridge 128 travels distally in the cartridge channel relative to the stopper 132 and the sliding body 116, thereby expelling the medicament from the medicament chamber, through the needle 120, and into the patient.

The locking rib 200 is disposed at the distal end of the cartridge channel so that when the medicament cartridge 128 reaches the end of its distal stroke (FIG. 10), the cartridge lip 204 distally passes the locking rib 200, thereby locking the medicament cartridge 128 relative to the sliding body 116. That is, the second locking mechanism (locking rib 200) engages the cartridge lip 204 and prevents movement of the medicament cartridge 128 with respect to the sliding body 116. Put another way, the second locking mechanism locks the medicament cartridge 128 relative to the sliding body 116 upon completion of the displacement of the medicament cartridge 128 relative to the sliding body 116. As used herein, locking an element relative to another element prevents subsequent relative displacement of the two elements. As additionally shown in FIG. 10, according to one embodiment, when the medicament cartridge 128 reaches the end of its distal stroke, the proximal surface of the medicament cartridge is substantially planar with the proximal surface of the sliding body 116. Such a configuration prevents a user from gaining a purchase on the medicament cartridge 128, and thereby prevents an attempt to proximally displace the medicament cartridge 128 relative to the sliding body 116.

Figure 11:
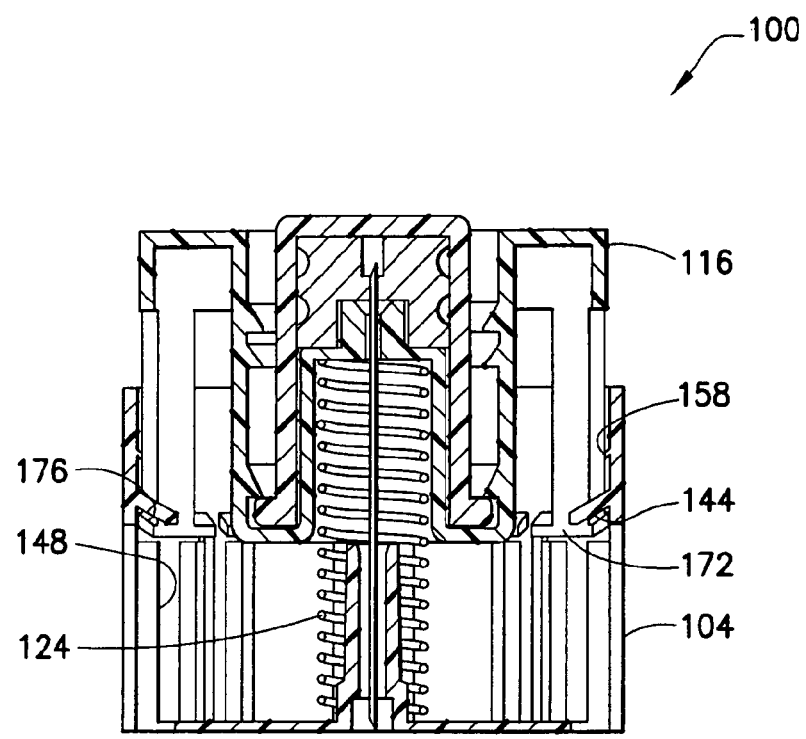

As shown in FIG. 11, subsequent to the administration of the medicament to the patient, the user releases the medicament cartridge 128 and the sliding body 116 (and the medicament cartridge 128 locked thereto) moves proximally with respect to the base 104 due to the force of the biasing member 124, thereby withdrawing the needle 120 from the patient and disposing the needle 120 completely within the device 100. More specifically, as the sliding body 116 moves proximally, the feet 172 slide proximally along the axial ribs 148. Upon passing the proximal ends of the axial ribs 148, the legs 168 and/or the feet 172 spring back radially outward into the locking spaces 152 and the proximal surfaces 176 of the feet 172 engage the distal angled surfaces 144 of the angled lips 136, thereby locking the sliding body 116 relative to the base 104. In other words, the distal angled surface 144 prevents proximal movement of the feet 172 and the proximal ends of the axial ribs 148 prevent distal movement of the feet 172. Put another way, the first locking mechanism and the locking feature interact to lock the sliding member 116 relative to the base 104 subsequent to retraction of the needle 120 into the device 100. In this third, or locked position of the sliding member 116, the needle 120 is again retracted entirely within the device 100. The third position of the sliding body 116 is distally displaced relative to the first position.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of the appended claims and equivalents thereof.

The invention claimed is:

1. An injection device, comprising:
a base having a proximal end and a surface disposed at a distal end thereof for contacting a patient's skin, the base comprising a first locking mechanism;
a sliding body slidably connected to the base, the sliding body comprising a locking feature and a second locking mechanism;
a double-ended needle fixed to the sliding body;
a biasing member for proximally biasing the sliding body with respect to the base, and for retracting the needle into the device subsequent to activation of the device;
a rigid medicament cartridge for holding a medicament, slidably connected to the sliding body, wherein the second locking mechanism locks the medicament cartridge relative to the sliding body upon completion of displacement of the medicament cartridge relative to the sliding body; and
a stopper slidably disposed within the medicament cartridge;
wherein the first locking mechanism and the locking feature interact to lock the sliding member relative to the base subsequent to retraction of the needle into the device.

2. The device according to claim 1, wherein the medicament cartridge is connectable to the sliding body.

3. The device according to claim 1, wherein the stopper is pierceable by the needle to establish communication with the medicament.

4. An injection device, comprising:
a base having a proximal end and a surface disposed at a distal end thereof for contacting a patient's skin, the base comprising a first locking mechanism;
a sliding body slidably connected to the base, the sliding body comprising a locking feature and a second locking mechanism;
a double-ended needle fixed to the sliding body;
a biasing member for proximally biasing the sliding body with respect to the base, and for retracting the needle into the device subsequent to activation of the device;
a medicament cartridge for holding a medicament, slidably connected to the sliding body, wherein the second locking mechanism locks the medicament cartridge relative to the sliding body upon completion of displacement of the medicament cartridge relative to the sliding body; and
a stopper slidably disposed within the medicament cartridge;
wherein the first locking mechanism and the locking feature interact to lock the sliding member relative to the base subsequent to retraction of the needle into the device; and
wherein the sliding body is moveable from a first position in which the needle is disposed entirely within the device, to a second position in which a portion of the needle extends outside of the device, and to a third position in which the needle is retracted entirely within the device, wherein the third position is distally displaced relative to the first position.

5. An injection device, comprising:
a base having a proximal end and a surface disposed at a distal end thereof for contacting a patient's skin, the base comprising a first locking mechanism;
a sliding body slidably connected to the base, the sliding body comprising a locking feature and a second locking mechanism;
a double-ended needle fixed to the sliding body;
a biasing member for proximally biasing the sliding body with respect to the base, and for retracting the needle into the device subsequent to activation of the device;
a medicament cartridge for holding a medicament, slidably connected to the sliding body, wherein the second locking mechanism locks the medicament cartridge relative to the sliding body upon completion of displacement of the medicament cartridge relative to the sliding body; and
a stopper slidably disposed within the medicament cartridge;
wherein the first locking mechanism and the locking feature interact to lock the sliding member relative to the base subsequent to retraction of the needle into the device; and
wherein the first locking mechanism comprises:
a plurality of angled lips disposed circumferentially about an interior of the base, the angled lips projecting radially inward and being angled distally, each angled lip having a proximal angled surface and a distal angled surface; and
a plurality of axial ribs circumferentially disposed about the interior of the base, the ribs being distally separated from the angled lips to define a locking space therebetween.

6. The device according to claim 5, wherein the plurality of axial ribs comprises a pair of axial ribs corresponding to each angled lip, each pair of axial ribs being circumferentially disposed on opposing sides of the corresponding angled lip.

7. The device according to claim 5, wherein the locking feature of the sliding body comprises a plurality of circumferentially disposed, distally depending, cantilevered legs, each leg having a pair of feet circumferentially protruding from a distal end thereof.

8. The device according to claim 7, wherein respective proximal surfaces of the feet are angled to correspond to the angle of the respective distal angled surfaces of the angled lips.

9. The device according to claim 7, wherein as the sliding body moves from a first position in which the needle is disposed entirely within the device to a second position in which a portion of the needle extends outside of the device, the feet engage the proximal angled surface of the angled lip, inwardly radially deflecting the legs and biasing the legs radially outward, and once the feet move distally past the angled lip, the feet move radially outward to engage and slide along the axial ribs.

10. The device according to claim 9, wherein as the sliding body moves from the second position to a third position in which the needle is retracted entirely within the device, the feet slide along the axial ribs until reaching proximal ends thereof and then move radially outward into the locking space.

11. An injection device, comprising:
a base having a proximal end and a surface disposed at a distal end thereof for contacting a patient's skin, the base comprising a first locking mechanism;
a sliding body slidably connected to the base, the sliding body comprising a locking feature and a second locking mechanism;
a double-ended needle fixed to the sliding body;
a biasing member for proximally biasing the sliding body with respect to the base, and for retracting the needle into the device subsequent to activation of the device;
a medicament cartridge for holding a medicament, slidably connected to the sliding body, wherein the second locking mechanism locks the medicament cartridge relative to the sliding body upon completion of displacement of the medicament cartridge relative to the sliding body; and
a stopper slidably disposed within the medicament cartridge;
wherein:
the first locking mechanism and the locking feature interact to lock the sliding member relative to the base subsequent to retraction of the needle into the device;
the medicament cartridge comprises a cartridge lip protruding radially outward from a distal end thereof; and
the second locking mechanism of the sliding body comprises a locking rib protruding radially inward, the locking rib being disposed adjacent a distal end of a cartridge channel of the sliding body in which the medicament cartridge travels; and
upon completion of displacement of the medicament cartridge relative to the sliding body, the cartridge lip distally passes the locking rib and the locking rib locks the medicament cartridge relative to the sliding body.

12. The device according to claim 11, wherein the cartridge channel comprises:
a connecting rib protruding radially inward; and
a holding rib protruding radially inward and being distally disposed relative to the connecting rib;
wherein the cartridge lip distally passes the connecting rib to connect the medicament cartridge to the sliding body;
wherein upon the cartridge lip distally passing the holding rib, the needle pierces the stopper; and
wherein a force required to distally displace the cartridge lip past the holding rib is greater than a force required to distally displace the cartridge lip past the connecting rib.

13. An injection device, comprising:
a base having a proximal end and a surface disposed at a distal end thereof for contacting a patient's skin, the base comprising a plurality of angled lips and a plurality of axial ribs, each plurality being disposed circumferentially about an interior of the base;
a sliding body slidably connected to the base, the sliding body comprising a holding rib protruding radially inward and a plurality of circumferentially disposed, distally depending, cantilevered legs, each leg having a pair of feet circumferentially protruding from a distal end thereof;
a double-ended needle fixed to the sliding body;
a biasing member for proximally biasing the sliding body with respect to the base, and for retracting the needle into the device subsequent to activation of the device;
a medicament cartridge for holding a medicament, the medicament cartridge being slidably connected to the sliding body and having a cartridge lip protruding radially outward from a distal end thereof, the cartridge lip being disposed adjacent to the holding rib prior to activation of the device; and
a stopper slidably disposed within the medicament cartridge;
wherein a force applied to the medicament cartridge to displace the cartridge lip distally past the holding lip exceeds a force applied to the medicament cartridge to displace the feet distally past the angled lips and drive the needle into a patient's skin.

14. The device according to claim 13, wherein:
each angled lip has a proximal angled surface and a distal angled surface; and
the plurality of axial ribs are distally separated from the angled lips to define a locking space therebetween.

15. The device according to claim 14, wherein respective proximal surfaces of the feet are angled to correspond to the angle of the respective distal angled surfaces of the angled lips.

16. The device according to claim 15, wherein the plurality of axial ribs comprises a pair of axial ribs corresponding to each angled lip, each pair of axial ribs being circumferentially disposed on opposing sides of the corresponding angled lip.

17. The device according to claim 16, wherein as the sliding body moves from a pre-activated position in which the needle is disposed entirely within the device to an activated position in which a portion of the needle extends outside of the device, the feet engage the proximal angled surfaces of the angled lips, inwardly radially deflecting the legs and biasing the legs radially outward, and once the feet move distally past the angled lip, the feet move radially outward to engage and slide along the axial ribs.

18. The device according to claim 17, wherein as the sliding body moves from the activated position to a locked position in which the needle is retracted entirely within the device, the feet slide along the axial ribs until reaching proximal ends thereof and then move radially outward into the locking space.

19. The device according to claim 18, wherein:
the sliding body comprises a locking rib protruding radially inward, the locking rib being disposed adjacent a distal end of a cartridge channel of the sliding body in which the medicament cartridge travels;
wherein upon completion of displacement of the medicament cartridge relative to the sliding body, the cartridge lip distally passes the locking rib and the locking rib locks the medicament cartridge relative to the sliding body.

20. A method for injecting a medicament in a patient using an injection device comprising a base, a sliding body slidably connected to the base, a double-ended needle fixed to the sliding body, a biasing member, a rigid medicament cartridge for holding a medicament, the medicament cartridge being slidably connected to the sliding body, and a stopper slidably disposed within the medicament cartridge, the method comprising:
pressing the medicament cartridge toward the patient's skin/injection site to sequentially:
distally displace the sliding body relative to the base, insert the needle into the patient, and compress the spring;

puncture the stopper with the needle to establish fluid communication between the needle and the medicament cartridge;

proximally displace the stopper relative to the medicament cartridge to eject the medicament from the medicament cartridge; and lock the medicament cartridge relative to the sliding body;

subsequent to ejecting the medicament from the medicament cartridge, ceasing pressure on the medicament cartridge to sequentially:

proximally displace the sliding body relative to the base to withdraw the needle from the patient due to the force of the spring; and lock the sliding member relative to the base to prevent reuse of the device.

* * * * *